US012622673B2

United States Patent
(12) United States Patent
Grinsteinner et al.

(10) Patent No.: US 12,622,673 B2
(45) Date of Patent: May 12, 2026

(54) ULTRASONIC PROBE

(71) Applicant: Ticona LLC, Florence, KY (US)

(72) Inventors: Darin Grinsteinner, Fort Mitchell, KY (US); Young Shin Kim, Cincinnati, OH (US)

(73) Assignee: Ticona LLC, Florence, KY (US)

( * ) Notice: Subject to any disclaimer, the term of this patent is extended or adjusted under 35 U.S.C. 154(b) by 294 days.

(21) Appl. No.: 16/921,994

(22) Filed: Jul. 7, 2020

(65) Prior Publication Data

US 2021/0015457 A1 Jan. 21, 2021

Related U.S. Application Data

(60) Provisional application No. 62/875,025, filed on Jul. 17, 2019.

(51) Int. Cl.

| | |
|---|---|
| ***A61B 8/00*** | (2006.01) |
| ***B06B 1/06*** | (2006.01) |
| ***C08G 63/60*** | (2006.01) |
| ***C08K 3/04*** | (2006.01) |

(52) U.S. Cl.

CPC .......... *A61B 8/4444* (2013.01); *A61B 8/4483* (2013.01); *B06B 1/0685* (2013.01); *C08G 63/605* (2013.01); *C08K 3/04* (2013.01); *C08K 2201/001* (2013.01); *C08K 2201/003* (2013.01)

(58) Field of Classification Search

CPC ... A61B 8/4444; A61B 8/4483; B06B 1/0685; C08G 63/605; C08K 3/04; C08K 2201/001; C08K 3/003

See application file for complete search history.

(56) References Cited

U.S. PATENT DOCUMENTS

| | | | |
|---|---|---|---|
| 4,161,470 | A | 7/1979 | Calundann |
| 5,616,680 | A | 4/1997 | Linstid, III |
| 6,022,491 | A | 2/2000 | Samuels et al. |
| 6,114,402 | A | 9/2000 | Smith |

(Continued)

FOREIGN PATENT DOCUMENTS

| | | | |
|---|---|---|---|
| AU | 2012201445 | B2 | 2/2014 |
| EP | 3795637 | A1 | 3/2021 |

(Continued)

OTHER PUBLICATIONS

EP Search Report for Application No. 20840809.6 dated Jun. 20, 2023, 8 pages.

(Continued)

*Primary Examiner* — James C Goloboy

(74) *Attorney, Agent, or Firm* — Dority & Manning, P.A.

(57) ABSTRACT

An ultrasonic probe that comprises an ultrasonic transducer that includes an array of transducer elements and an attenuation material is provided. The attenuation material comprises a polymer composition that includes a liquid crystalline polymer and a thermally conductive particulate material. The liquid crystalline polymer has a melting temperature of about 270° C. or more and a melt viscosity of about 500 Pa-s or less as determined at a temperature of 45° C. above the melting temperature and shear rate of 400 $s^{-1}$ in accordance with ISO Test No. 11443:2005, and the polymer composition also has a through-plane conductivity of about 0.2 W/m-K or more.

22 Claims, 3 Drawing Sheets

(56) References Cited

U.S. PATENT DOCUMENTS

| | | | |
|---|---|---|---|
| 6,514,611 B1 | 2/2003 | Shepherd et al. | |
| 7,808,157 B2 | 10/2010 | Oakley et al. | |
| 8,556,030 B2 | 10/2013 | Oakley et al. | |
| 9,402,599 B2 | 8/2016 | Okuda | |
| 10,710,116 B2 | 7/2020 | Chartrand et al. | |
| 11,466,130 B2 | 10/2022 | Grinsteinner | |
| 2013/0200297 A1* | 8/2013 | Saga | H05K 7/20481 252/74 |
| 2016/0145411 A1 | 5/2016 | Uibel et al. | |
| 2016/0152801 A1* | 6/2016 | Yu | C09K 19/54 524/135 |
| 2019/0307424 A1* | 10/2019 | Kitagaki | B06B 1/0622 |
| 2020/0253584 A1 | 8/2020 | Morimoto | |

FOREIGN PATENT DOCUMENTS

| | | |
|---|---|---|
| WO | WO 2004/058851 A1 | 7/2004 |
| WO | WO 2004/058915 A1 | 7/2004 |
| WO | WO 2015/145402 A1 | 10/2015 |

OTHER PUBLICATIONS

International Search Report and Written Opinion for PCT/US2020/040951 dated Jan. 19, 2021, 14 pages.

Information Disclosure Statement filed by applicant Oct. 3, 2025.

* cited by examiner

ULTRASONIC PROBE

RELATED APPLICATION

The present application claims priority to U.S. Provisional Application Ser. No. 62/875,025, filed on Jul. 17, 2019, which is incorporated herein in its entirety by reference thereto.

BACKGROUND OF THE INVENTION

Ultrasound imaging probes continue to enjoy widespread use in the medical field. By way of example, ultrasound probes are utilized for a wide variety of external, laparoscopic, endoscopic and intravascular imaging applications. The ultrasound images provided by imaging probes may, for example, be used for diagnostic purposes. The probes typically include a plurality of parallel piezoelectric transducer elements arranged along a longitudinal axis, with each element interconnected to a pair of electrodes. An electronic circuit excites the transducer elements causing them to emit ultrasonic energy. The transducer elements then convert the received ultrasonic energy into electrical signals, which may then be processed and used to generate images. Typically, the transducers include an active layer of a piezoelectric material with an acoustic face from which acoustic signals are emitted. An acoustic attenuation member is also generally disposed on the back surface of the active layer to dampen undesirable acoustic signals (e.g., signals that may emanate from and be reflected back to the rear face of the transducer), which would otherwise interfere with the acoustic signals received at the acoustic face. Unfortunately, due to the increased complexity of most probe designs, power consumption is increased, which in turn leads to an increase in the amount of heat that is produced by the probe. This increased production of heat can be a problem due to the fact most acoustic attenuation members are not highly heat sensitive. Over time, this can ultimately lead to a malfunction of the camera sensor.

As such, a need exists for an improved ultrasonic probe having a higher degree of heat sensitivity.

SUMMARY OF THE INVENTION

In accordance with one embodiment of the present invention, an ultrasonic probe is disclosed that comprises an ultrasonic transducer that includes an array of transducer elements capable of converting electrical energy to ultrasonic acoustic energy for emission towards a region of interest and an attenuation material that is capable of inhibiting the return of the ultrasonic acoustic energy back towards the ultrasonic transducer after emission towards the region of interest. The attenuation material comprises a polymer composition that includes a liquid crystalline polymer and a thermally conductive particulate material. The liquid crystalline polymer has a melting temperature of about 270° C. or more and a melt viscosity of about 500 Pa-s or less as determined at a temperature of 45° C. above the melting temperature and shear rate of 400 $s^{-1}$ in accordance with ISO Test No. 11443:2005, and the polymer composition also has a through-plane conductivity of about 0.2 W/m-K or more.

Other features and aspects of the present invention are set forth in greater detail below.

BRIEF DESCRIPTION OF THE FIGURES

A full and enabling disclosure of the present invention, including the best mode thereof to one skilled in the art, is set forth more particularly in the remainder of the specification, including reference to the accompanying figures, in which.

DETAILED DESCRIPTION

Figure 1:
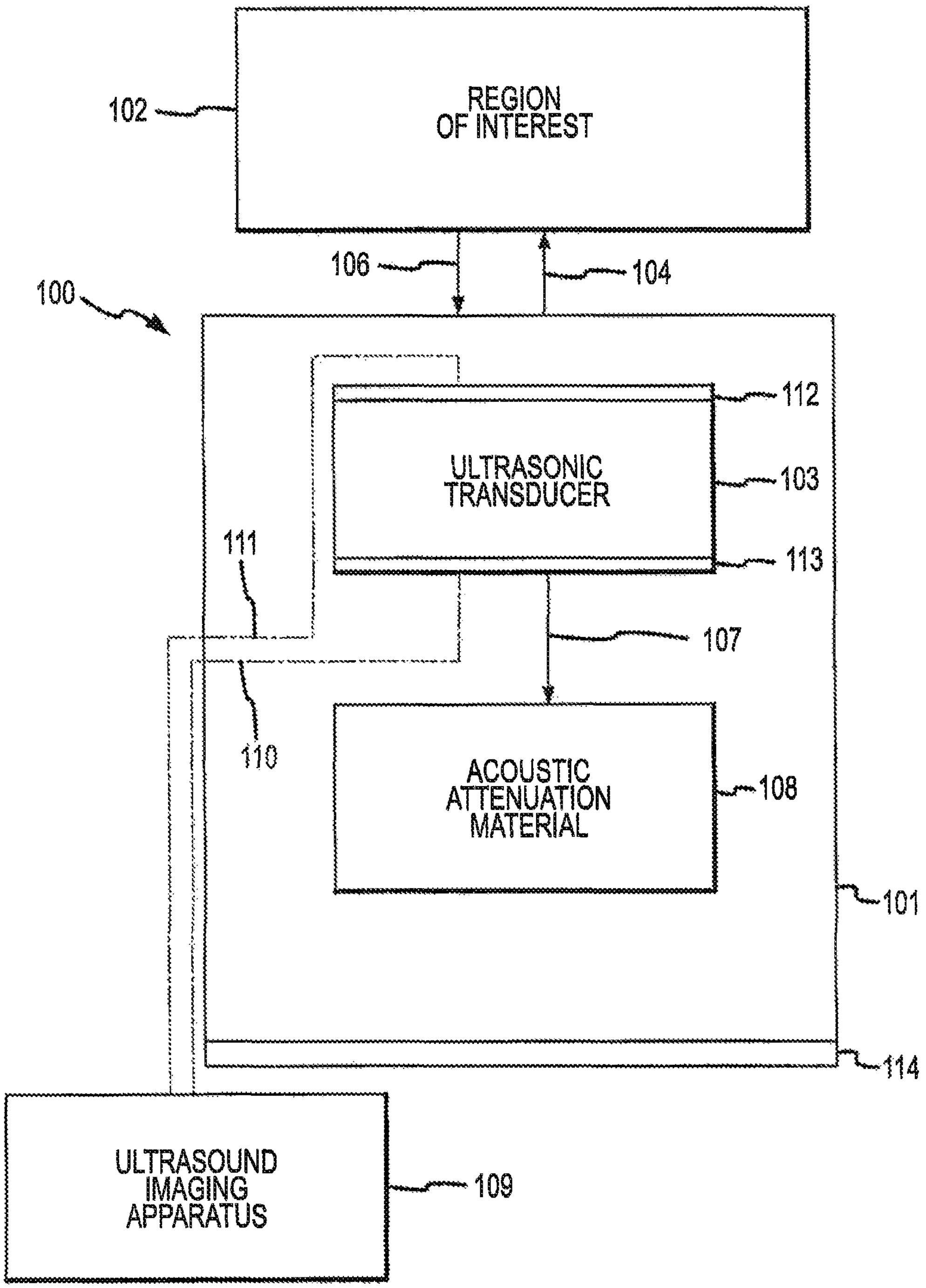
FIG. 1 is a schematic diagram of an embodiment of an ultrasound probe and a region of interest.

It is to be understood by one of ordinary skill in the art that the present discussion is a description of exemplary embodiments only, and is not intended as limiting the broader aspects of the present invention.

Generally speaking, the present invention is directed to an ultrasonic probe that contains an ultrasonic transducer and an attenuation material that is capable of attenuating acoustic energy incident upon the material, such as energy having a frequency between 100 kHz and 100 MHz. The attenuation material includes a polymer composition, which contains a liquid crystalline polymer and thermally conductive particulate material. By selectively controlling the nature of the components in the polymer composition and their relative concentration, the resulting composition is capable of serving as an effective acoustic attenuation material, but also exhibit good thermal properties that allow for heat transfer so that "hot spots" can be quickly eliminated and the overall temperature of the part can be lowered during use. More particularly, the composition exhibits a through-plane thermal conductivity of about 0.2 W/m-K or more, in some embodiments about 0.4 W/m-K or more, in some embodiments about 0.5 W/m-K or more, in some embodiments from about 1 to about 25 W/m-K, in some embodiments from about 2 to about 20 W/m-k, and in some embodiments, from about 4 to about 15 W/m-K, as determined in accordance with ASTM E 1461-13.

Various embodiments of the present invention will now be described in more detail.

I. Polymer Composition

A. Liquid Crystalline Polymer

As indicated above, the liquid crystalline polymer employed in the polymer matrix has a melting temperature within a carefully controlled range of from about 270° C. to about 400° C., in some embodiments from about 280° C. to about 380° C., in some embodiments from about 290° C. to about 370° C., and in some embodiments, from about 300° C. to about 350° C. One particularly suitable liquid crystalline polymer contains the following repeating units (1) to (3):

(1)

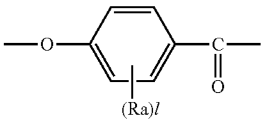

(2)

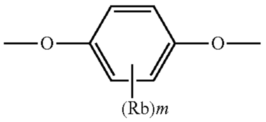

-continued (3)

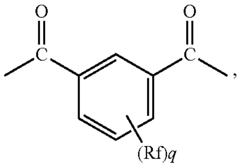

wherein,

Ra, Rb, and Rf are independently alkenyl, alkyl, alkynyl, aryl, heteroaryl, cycloalkyl, heterocyclyl, halo, or haloalkyl; and l, m, and q are independently an integer from 0 to 4, in some embodiments from 0 to 2, and in some embodiments, from 0 to 1.

In certain embodiments, the repeating units (1) may be derived from 4-hydroxybenzoic acid ("HBA") (l is 0), the repeating units (2) may be derived from hydroquinone ("HQ") (m is 0), and/or the repeating units (3) may be derived from isophthalic acid ("IA") (q is 0).

By selectively controlling the nature and relative proportion of the repeating units (1)-(3), the present inventors have discovered the resulting polymer may not only achieve a melting temperature within the range noted above, but also still achieve a significant degree of chain entanglement such that the polymer exhibits good melt strength, which enables it to be readily employed in the ultrasonic probe of the present invention. For example, the repeating units (1) may constitute from about 40 mole % to about 80 mole %, in some embodiments from about 50 mole % to about 70 mole %, and in some embodiments, from about 55 mole % to about 65 mole % of the polymer. Likewise, the repeating units (2) and (3) may each constitute from about 1 mole % to about 20 mole %, in some embodiments from about 2 mole % to about 15 mole %, and in some embodiments, from about 5 mole % to about 10 mole % of the polymer. Regardless of the exact molar amount employed, the molar ratio of repeating units (2) to the repeating units (3) may be selectively controlled so that it is from about 0.8 to about 2, in some embodiments from about 0.9 to about 1.6, and in some embodiments, from about 1 to about 1.5. In some cases, the repeating units (2) are used in a molar amount greater than the repeating units (3) such that the molar ratio is greater than 1.

Of course, it should be understood that other repeating units may also be employed in the polymer.

(4)

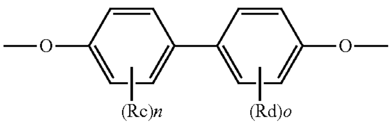

(5)

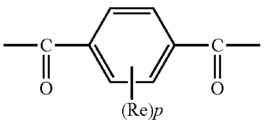

wherein,

Rc, Rd, and Re are independently alkenyl, alkyl, alkynyl, aryl, heteroaryl, cycloalkyl, heterocyclyl, halo, or haloalkyl; and n, o, and p are independently an integer from 0 to 4, in some embodiments from 0 to 2, and in some embodiments, from 0 to 1.

In certain embodiments, the repeating units (4) may be derived from 4,4'-biphenol ("BP") (n and o are 0) and/or the repeating units (5) may be derived from terephthalic acid ("TA") (p is 0).

The repeating units (4) and (5) may each constitute from about 5 mole % to about 30 mole %, in some embodiments from about 6 mole % to about 25 mole %, and in some embodiments, from about 8 mole % to about 15 mole % of the polymer. Regardless of the exact molar amount employed, the molar ratio of repeating units (5) to the repeating units (4) may be selectively controlled so that it is from about 0.8 to about 2, in some embodiments from about 0.9 to about 1.6, and in some embodiments, from about 1 to about 1.5. In some cases, the repeating units (5) are used in a molar amount greater than the repeating units (4) such that the molar ratio is greater than 1.

Still other repeating units may also be employed in the polymer. For example, other aromatic hydroxycarboxylic repeating units may also be employed that are derived from aromatic hydroxycarboxylic acids other than HBA, such as, 4-hydroxy-4'-biphenylcarboxylic acid; 2-hydroxy-6-naphthoic acid ("HNA"); 2-hydroxy-5-naphthoic acid; 3-hydroxy-2-naphthoic acid; 2-hydroxy-3-naphthoic acid; 4'-hydroxyphenyl-4-benzoic acid; 3'-hydroxyphenyl-4-benzoic acid; 4'-hydroxyphenyl-3-benzoic acid, etc., as well as alkyl, alkoxy, aryl and halogen substituents thereof, and combination thereof. Likewise, other aromatic dicarboxylic repeating units may be employed that are derived from aromatic dicarboxylic acids other than TA and IA, such as 2,6-naphthalenedicarboxylic acid ("NDA"), diphenyl ether-4,4'-dicarboxylic acid, 1,6-naphthalenedicarboxylic acid, 2,7-naphthalenedicarboxylic acid, 4,4'-dicarboxybiphenyl, bis(4-carboxyphenyl)ether, bis(4-carboxyphenyl)butane, bis(4-carboxyphenyl)ethane, bis(3-carboxyphenyl)ether, bis(3-carboxyphenyl)ethane, etc., as well as alkyl, alkoxy, aryl and halogen substituents thereof, and combinations thereof. Aromatic diol repeating units may also be employed that are derived from aromatic diols other than HQ and BP, such as resorcinol, 2,6-dihydroxynaphthalene, 2,7-dihydroxynaphthalene, 1,6-dihydroxynaphthalene, 4,4'-dihydroxybiphenyl (or 4,4'-biphenol), 3,3'-dihydroxybiphenyl, 3,4'-dihydroxybiphenyl, 4,4'-dihydroxybiphenyl ether, bis(4-hydroxyphenyl)ethane, etc., as well as alkyl, alkoxy, aryl and halogen substituents thereof, and combinations thereof. Repeating units may also be employed, such as those derived from aromatic amides (e.g., acetaminophen ("APAP")) and/or aromatic amines (e.g., 4-aminophenol ("AP"), 3-aminophenol, 1,4-phenylenediamine, 1,3-phenylenediamine, etc.). It should also be understood that various other monomeric repeating units may be incorporated into the polymer. For instance, in certain embodiments, the polymer may contain one or more repeating units derived from non-aromatic monomers, such as aliphatic or cycloaliphatic hydroxycarboxylic acids, dicarboxylic acids (e.g., cyclohexane dicarboxylic acid), diols, amides, amines, etc. Of course, in other embodiments, the polymer may be "wholly aromatic" in that it lacks repeating units derived from non-aromatic (e.g., aliphatic or cycloaliphatic) monomers.

Although not necessarily required, it may be desired that the liquid crystalline polymer contains a low content of repeating units derived from naphthenic hydroxycarboxylic acids and naphthenic dicarboxylic acids, such as NDA, HNA, or combinations thereof. That is, the total amount of repeating units derived from naphthenic hydroxycarboxylic and/or dicarboxylic acids (e.g., NDA, HNA, or a combination of HNA and NDA) is typically less than about 10 mol. %, in some embodiments less than about 5 mol. %, and in some embodiments, less than about 1 mol. % of the polymer. The liquid crystalline polymer may also contain a low content of repeating units derived from aromatic amides and aromatic amines, such as APAP, AP, or combinations thereof. That is, the total amount of repeating units derived from aromatic amides and/or amines (e.g., APAP, AP, or a combination of APAP and AP) is typically less than about 10 mol. %, in some embodiments less than about 5 mol. %, and in some embodiments, less than about 1 mol. % of the polymer. In particular embodiments, the polymer contains 0 mol. % of naphthenic hydroxycarboxylic acids (e.g., HNA), 0 mol. % of naphthenic dicarboxylic acids (e.g., NDA), 0 mol. % of aromatic amides (e.g., APAP), and/or 0 mol. % of aromatic amines (e.g., AP). In fact, the liquid crystalline polymer may be formed entirely from the repeating units (1)-(5) if so desired such that the total molar percentage of the repeating units (1)-(5) equals 100%.

The liquid crystalline polymer may be synthesized in a melt polymerization process. The process may involve initially introducing the monomer(s) used to form the repeating units (e.g., HBA, IA, HQ, TA, and/or BP) into a reactor vessel to initiate a polycondensation reaction. The particular conditions and steps employed in such reactions are well known, and may be described in more detail in U.S. Pat. No. 4,161,470 to Calundann; U.S. Pat. No. 5,616,680 to Linstid, III, et al.; U.S. Pat. No. 6,114,492 to Linstid, III, et al.; U.S. Pat. No. 6,514,611 to Shepherd, et al.; and WO 2004/058851 to Waggoner. The vessel employed for the reaction is not especially limited, although it is typically desired to employ one that is commonly used in reactions of high viscosity fluids. Examples of such a reaction vessel may include a stirring tank-type apparatus that has an agitator with a variably-shaped stirring blade, such as an anchor type, multistage type, spiral-ribbon type, screw shaft type, etc., or a modified shape thereof. Further examples of such a reaction vessel may include a mixing apparatus commonly used in resin kneading, such as a kneader, a roll mill, a Banbury mixer, etc.

If desired, the reaction may proceed through the acetylation of the monomers as known the art. This may be accomplished by adding an acetylating agent (e.g., acetic anhydride) to the monomers. Acetylation is generally initiated at temperatures of about 90° C. During the initial stage of the acetylation, reflux may be employed to maintain vapor phase temperature below the point at which acetic acid byproduct and anhydride begin to distill. Temperatures during acetylation typically range from between 90° C. to 150° C., and in some embodiments, from about 110° C. to about 150° C. If reflux is used, the vapor phase temperature typically exceeds the boiling point of acetic acid, but remains low enough to retain residual acetic anhydride. For example, acetic anhydride vaporizes at temperatures of about 140° C. Thus, providing the reactor with a vapor phase reflux at a temperature of from about 110° C. to about 130° C. is particularly desirable. To ensure substantially complete reaction, an excess amount of acetic anhydride may be employed. The amount of excess anhydride will vary depending upon the particular acetylation conditions employed, including the presence or absence of reflux. The use of an excess of from about 1 to about 10 mole percent of acetic anhydride, based on the total moles of reactant hydroxyl groups present is not uncommon.

Acetylation may occur in in a separate reactor vessel, or it may occur in situ within the polymerization reactor vessel. When separate reactor vessels are employed, one or more of the monomers may be introduced to the acetylation reactor and subsequently transferred to the polymerization reactor. Likewise, one or more of the monomers may also be directly introduced to the reactor vessel without undergoing pre-acetylation.

In addition to the monomers and optional acetylating agents, other components may also be included within the reaction mixture to help facilitate polymerization. For instance, a catalyst may be optionally employed, such as metal salt catalysts (e.g., magnesium acetate, tin(I) acetate, tetrabutyl titanate, lead acetate, sodium acetate, potassium acetate, etc.) and organic compound catalysts (e.g., N-methylimidazole). Such catalysts are typically used in amounts of from about 50 to about 500 parts per million based on the total weight of the recurring unit precursors. When separate reactors are employed, it is typically desired to apply the catalyst to the acetylation reactor rather than the polymerization reactor, although this is by no means a requirement.

The reaction mixture is generally heated to an elevated temperature within the polymerization reactor vessel to initiate melt polycondensation of the reactants. Polycondensation may occur, for instance, within a temperature range of from about 270° C. to about 400° C. For instance, one suitable technique for forming the polymer may include charging precursor monomers and acetic anhydride into the reactor, heating the mixture to a temperature of from about 90° C. to about 150° C. to acetylize the monomers (e.g., forming acetoxy), and then increasing the temperature to a temperature of from about 270° C. to about 400° C. to carry out melt polycondensation. As the final polymerization temperatures are approached, volatile byproducts of the reaction (e.g., acetic acid) may also be removed so that the desired molecular weight may be readily achieved. The reaction mixture is generally subjected to agitation during polymerization to ensure good heat and mass transfer, and in turn, good material homogeneity. The rotational velocity of the agitator may vary during the course of the reaction, but typically ranges from about 10 to about 100 revolutions per minute ("rpm"), and in some embodiments, from about 20 to about 80 rpm. To build molecular weight in the melt, the polymerization reaction may also be conducted under vacuum, the application of which facilitates the removal of volatiles formed during the final stages of polycondensation. The vacuum may be created by the application of a suctional pressure, such as within the range of from about 5 to about 30 pounds per square inch ("psi"), and in some embodiments, from about 10 to about 20 psi.

Following melt polymerization, the molten polymer may be discharged from the reactor, typically through an extrusion orifice fitted with a die of desired configuration, cooled, and collected. Commonly, the melt is discharged through a perforated die to form strands that are taken up in a water bath, pelletized and dried. The resin may also be in the form of a strand, granule, or powder.

Regardless of the particular method employed, the resulting polymer may have a relatively low melt viscosity, such as from about 25 to about 350 Pa-s, in some embodiments from about 30 to about 305 Pa-s, and in some embodiments, from about 35 to about 250 Pa-s, determined at a shear rate of 400 seconds$^{-1}$. Melt viscosity may be determined in accordance with ISO Test No. 11443:2005 at about 45° C. higher than the melting temperature of the polymer (e.g., at 350° C. for a polymer with a melting temperature of 305° C.).

B. Thermally Conductive Particulate Material

To help achieve the desired thermal properties, the polymer composition also contains a thermally conductive particulate material. The particulate material typically has an average size (e.g., diameter) of about 100 to about 2,000 micrometers, in some embodiments from about 250 to about 1,400 micrometers, in some embodiments from about 300 to about 1,300 micrometers, and in some embodiments, from about 400 to about 1,200 micrometers, such as determined using laser diffraction techniques in accordance with ISO 13320:2009 (e.g., with a Horiba LA-960 particle size distribution analyzer). The thermally conductive particulate material may also have a narrow size distribution. That is, at least about 70% by volume of the particles, in some embodiments at least about 80% by volume of the particles, and in some embodiments, at least about 90% by volume of the particles may have a size within the ranges noted above. In certain embodiments, the particulate material may have a "flake" shape in that it has a relatively high aspect ratio (e.g., average length or diameter divided by average thickness), such as about 4:1 or more, in some embodiments about 8:1 or more, and in some embodiments, from about 10:1 to about 2000:1. The average thickness may, for instance, be about 10 micrometers or less, in some embodiments from about 0.01 micrometers to about 8 micrometers, and in some embodiments, from about 0.05 micrometers to about 5 micrometers. The specific surface area of the material may also be relatively high, such as about 0.5 $m^2/g$ or more, in some embodiments about 1 $m^2/g$ or more, and in some embodiments, from about 2 to about 40 $m^2/g$. The specific surface area can be determined according to standard methods such as by the physical gas adsorption method (B.E.T. method) with nitrogen as the adsorption gas, as is generally known in the art and described by Brunauer, Emmet, and Teller (J. Amer. Chem. Soc., vol. 60, February, 1938, pp. 309-319). The particulate material may also have a powder tap density of from about 0.2 to about 1.0 $g/cm^3$, in some embodiments from about 0.3 to about 0.9 $g/cm^3$, and in some embodiments, from about 0.4 to about 0.8 $g/cm^3$, such as determined in accordance with ASTM B527-15.

Further, the thermally conductive particulate material may have a high intrinsic thermal conductivity, such as about 50 W/m-K or more, in some embodiments about 100 W/m-K or more, and in some embodiments, about 150 W/m-K or more. Examples of such materials may include, for instance, boron nitride (BN), aluminum nitride (AlN), magnesium silicon nitride ($MgSiN_2$), graphite (e.g., expanded graphite), silicon carbide (SiC), carbon nanotubes, carbon black, metal oxides (e.g., zinc oxide, magnesium oxide, beryllium oxide, zirconium oxide, yttrium oxide, etc.), metallic powders (e.g., aluminum, copper, bronze, brass, etc.), etc., as well as combinations thereof. Graphite is particularly suitable for use in the polymer composition of the present invention. In fact, in certain embodiments, graphite may constitute a majority of the thermally conductive particulate material employed in the polymer composition, such as about 50 wt. % or more, in some embodiments, about 70 wt. % or more, and in some embodiments, from about 90 wt. % to 100 wt. % of the thermally conductive particulate material.

The thermally conductive particulate material is typically employed in the polymer composition in an amount of from about 50 to about 200 parts, in some embodiments from about 70 to about 180 parts, and in some embodiments, from about 100 to about 150 parts by weight per 100 parts of the liquid crystalline polymer. For example, the thermally conductive particulate material may constitute from about 25 wt. % to about 70 wt. %, in some embodiments from about 30 wt. % to about 65 wt. %, and in some embodiments, from about 40 wt. % to about 60 wt. % of the polymer composition. Liquid crystalline polymers may likewise constitute from about 30 wt. % to about 75 wt. %, in some embodiments from about 35 wt. % to about 70 wt. %, and in some embodiments, from about 40 wt. % to about 60 wt. % of the polymer composition.

C. Optional Components

A wide variety of other components can also be included in the polymer composition, such as flow modifiers, lubricants, pigments, antioxidants, stabilizers, surfactants, waxes, flame retardants, anti-drip additives, nucleating agents (e.g., boron nitride), inorganic particle fillers (e.g., talc, mica, etc.), inorganic fibrous fillers (e.g., glass fibers), and other materials added to enhance properties and processability, and other materials added to enhance properties and processability. Lubricants, for example, may be employed in the polymer composition that are capable of withstanding the processing conditions of the liquid crystalline polymer without substantial decomposition. Examples of such lubricants include fatty acids esters, the salts thereof, esters, fatty acid amides, organic phosphate esters, and hydrocarbon waxes of the type commonly used as lubricants in the processing of engineering plastic materials, including mixtures thereof. Suitable fatty acids typically have a backbone carbon chain of from about 12 to about 60 carbon atoms, such as myristic acid, palmitic acid, stearic acid, arachic acid, montanic acid, octadecinic acid, parinric acid, and so forth. Suitable esters include fatty acid esters, fatty alcohol esters, wax esters, glycerol esters, glycol esters and complex esters. Fatty acid amides include fatty primary amides, fatty secondary amides, methylene and ethylene bisamides and alkanolamides such as, for example, palmitic acid amide, stearic acid amide, oleic acid amide, N,N'-ethylenebisstearamide and so forth. Also suitable are the metal salts of fatty acids such as calcium stearate, zinc stearate, magnesium stearate, and so forth; hydrocarbon waxes, including paraffin waxes, polyolefin and oxidized polyolefin waxes, and microcrystalline waxes. Particularly suitable lubricants are acids, salts, or amides of stearic acid, such as pentaerythritol tetrastearate, calcium stearate, or N,N'-ethylenebisstearamide. When employed, the lubricant(s) typically constitute from about 0.05 wt. % to about 1.5 wt. %, and in some embodiments, from about 0.1 wt. % to about 0.5 wt. % (by weight) of the polymer composition.

II. Formation

The components of the polymer composition (e.g., liquid crystalline polymer(s), thermally conductive particulate material(s), etc.) may be melt processed or blended together. The components may be supplied separately or in combination to an extruder that includes at least one screw rotatably mounted and received within a barrel (e.g., cylindrical barrel) and may define a feed section and a melting section located downstream from the feed section along the length of the screw. The extruder may be a single screw or twin screw extruder. The speed of the screw may be selected to achieve the desired residence time, shear rate, melt processing temperature, etc. For example, the screw speed may range from about 50 to about 800 revolutions per minute ("rpm"), in some embodiments from about 70 to about 150 rpm, and in some embodiments, from about 80 to about 120 rpm. The apparent shear rate during melt blending may also range from about 100 $seconds^{-1}$ to about 10,000 $seconds^{-1}$, in some embodiments from about 500 $seconds^{-1}$ to about 5000 $seconds^{-1}$, and in some embodiments, from about 800 $seconds^{-1}$ to about 1200 $seconds^{-1}$. The apparent shear rate is equal to 4 $Q/\pi R^3$, where Q is the volumetric flow rate ("$m^3/s$") of the polymer melt and R is the radius ("m") of the capillary (e.g., extruder die) through which the melted polymer flows.

Regardless of the particular manner in which it is formed, the resulting polymer composition can possess excellent thermal properties. For example, the melt viscosity of the polymer composition may be low enough so that it can readily flow into the cavity of a mold having small dimensions. In one particular embodiment, the polymer composition may have a melt viscosity of about 500 Pa-s or less, in some embodiments from about 50 to about 450 Pa-s, in some embodiments from about 60 to about 400 Pa-s, in some embodiments from about 80 to about 370 Pa-s, and in some embodiments, from about 150 to about 350 Pa-s, determined at a shear rate of 400 $seconds^{-1}$. Melt viscosity may be determined in accordance with ISO Test No. 11443:2005 at a temperature that is 45° C. higher than the melting temperature of the composition (e.g., about 350° C.).

Of course in addition to those noted above, the polymer composition may also exhibit other good strength properties. For example, the composition may exhibit a Charpy unnotched impact strength of about 1 $kJ/m^2$, in some embodiments from about 2 to about 40 $kJ/m^2$, and in some embodiments, from about 3 to about 30 $kJ/m^2$, measured at 23° C. according to ISO Test No. 179-1:2010 (technically equivalent to ASTM D256-10e1). The composition may also exhibit a tensile strength of from about 10 to about 500 MPa, in some embodiments from about 20 to about 400 MPa, and in some embodiments, from about 30 to about 350 MPa; tensile break strain of about 0.3% or more, in some embodiments from about 0.5% to about 15%, and in some embodiments, from about 0.6% to about 10%; and/or tensile modulus of from about 4,000 MPa to about 30,000 MPa, in some embodiments from about 6,000 MPa to about 25,000 MPa, and in some embodiments, from about 7,000 MPa to about 20,000 MPa. The tensile properties may be determined in accordance with ISO Test No. 527:2012 (technically equivalent to ASTM D638-14) at 23° C. The composition may also exhibit a flexural strength of from about 30 to about 500 MPa, in some embodiments from about 40 to about 400 MPa, and in some embodiments, from about 50 to about 350 MPa and/or a flexural break strain of about 0.3% or more, in some embodiments from about 0.4% to about 15%, and in some embodiments, from about 0.6% to about 10%. The flexural properties may be determined in accordance with ISO Test No. 178:2010 (technically equivalent to ASTM D790-10) at 23° C. The composition may also exhibit a deflection temperature under load (DTUL) of about 180° C. or more, and in some embodiments, from about 190° C. to about 280° C., as measured according to ASTM D648-07 (technically equivalent to ISO Test No. 75-2:2013) at a specified load of 1.8 MPa.

III. Ultrasonic Probe

As indicated above, the polymer composition of the present invention is employed in at least a portion of an ultrasonic transducer probe. The probe may be used to generate two-dimensional and/or three-dimensional imaging, may be a linear, convex (curved), phased (sector), single, or TV-type probe. Generally speaking, the ultrasonic probe contains at least one ultrasonic transducer that includes an array of transducer elements capable of converting electrical energy to ultrasonic acoustic energy for emission towards a region of interest. The probe also contains an attenuation material that is capable of inhibiting the return of the ultrasonic acoustic energy back towards the ultrasonic transducer after emission towards the region of interest.

The particular configuration of the probe may vary as is known to those skilled in the art. Referring to FIG. 1, for example, one embodiment of an ultrasonic probe 100 is shown that includes at least one ultrasonic transducer 103. The ultrasonic transducer 103 may be a mechanically active layer operable to convert electrical energy to mechanical (e.g., acoustic) energy and/or convert mechanical energy into electrical energy. For example, the ultrasonic transducer 103 may be operable to convert electrical signals from the ultrasound imaging apparatus 109 into ultrasonic acoustic energy. Furthermore, the ultrasonic transducer 103 may be operable to convert received ultrasonic acoustic energy into electrical signals. The ultrasonic transducer 103 may contain at least one ground electrode 112 and at least one signal electrode 113. The signal electrode 113 and the ground electrode 112 may be electrically interconnected to the ultrasound imaging apparatus 109 by at least one signal connection 110 (e.g., at least one signal wire) and at least one ground connection 111 (e.g., at least one ground wire), respectively. The ultrasonic transducer 103 may also contain an array of individual transducer elements (not shown) that may each be electrically connected to the ultrasound imaging apparatus 109 via a signal connection and a ground connection. The array may be a one-dimensional array that includes a single row of individual transducer elements, or a multi-dimensional array (e.g., two-dimensional) that includes individual transducer elements arranged, for example, in multiple columns and multiple rows. Ground connections of the entire array may be aggregated and be electrically connected to the ultrasound imaging apparatus 109 through a single ground connection.

To generate an ultrasound image, the ultrasound imaging apparatus 109 may send electrical signals to the ultrasonic transducer 103, which in turn may convert the electrical energy to ultrasonic acoustic energy 104 for emission towards a region of interest 102. The region of interest 102 may be an internal structure of a patient, such as an organ. The structure within the region of interest 102 may reflect a portion of the acoustic energy 106 back toward the ultrasonic transducer 103. The reflected acoustic energy 106 may be converted to electrical signals by the ultrasonic transducer 103, which may be sent to the ultrasound imaging apparatus 109 where the signals may be processed and an image of the region of interest 102 may be generated. The process of converting the electrical signals from the ultrasound imaging apparatus 109 into ultrasonic acoustic energy 104 may also produce additional acoustic energy 107 directed in directions other than toward the region of interest 102. This additional acoustic energy 107 may reflect off of various structures, such as the housing 101 of the ultrasound probe 100, and return to the ultrasonic transducer 103 where it may be converted to electrical signals. The electrical signals from the reflected additional acoustic energy 107 may interfere with the electrical signals from the reflected acoustic energy 106. Such interference may result in image quality degradation.

Thus, to reduce interference from the reflected additional acoustic energy 107, an acoustic attenuation material 108 may be included in the ultrasound probe 100. The acoustic attenuation material 108 may be interconnected to the ultrasonic transducer 103 along a surface of the ultrasonic transducer 103 opposite from the surface of the ultrasonic transducer 103 facing the region of interest 102 (e.g., a back surface of the ultrasonic transducer 103). The acoustic attenuation material 108 may prevent a substantial amount of the additional acoustic energy 107 from returning to the back surface of the ultrasonic transducer 103. The acoustic attenuation material 108 may also reduce the amount of acoustic energy reaching the back surface of the ultrasonic transducer 103 from other sources. In this regard, the acoustic attenuation material 108 may provide for reduced interference and enhanced image quality. In embodiments where the acoustic attenuation material 108 is connected directly to the ultrasonic transducer 103, the signal connection 110 may pass through the acoustic attenuation material 108.

The acoustic attenuation material 108 may also be positioned in other locations within the ultrasound probe 100 to attenuate acoustic energy within the ultrasound probe 100. For example, an amount of acoustic attenuation material 114 may be placed against the housing 101 or even form all or a part of the housing 101 to dampen (e.g., absorb) acoustic energy that may otherwise reflect off of an inner surface of the housing 101 and reduce image quality. Although illustrated as lining one entire side of the inside of the housing 101 in FIG. 1, it should also be understood that the acoustic attenuation material 114 may be placed along any surface or portion thereof of the housing 101 where it may be beneficial to attenuate acoustic energy. The acoustic attenuation material 114 may also be located adjacent to other structures within the ultrasound probe 100 (e.g., circuit boards) to attenuate acoustic energy that could otherwise reflect off of those other structures.

Figure 2:
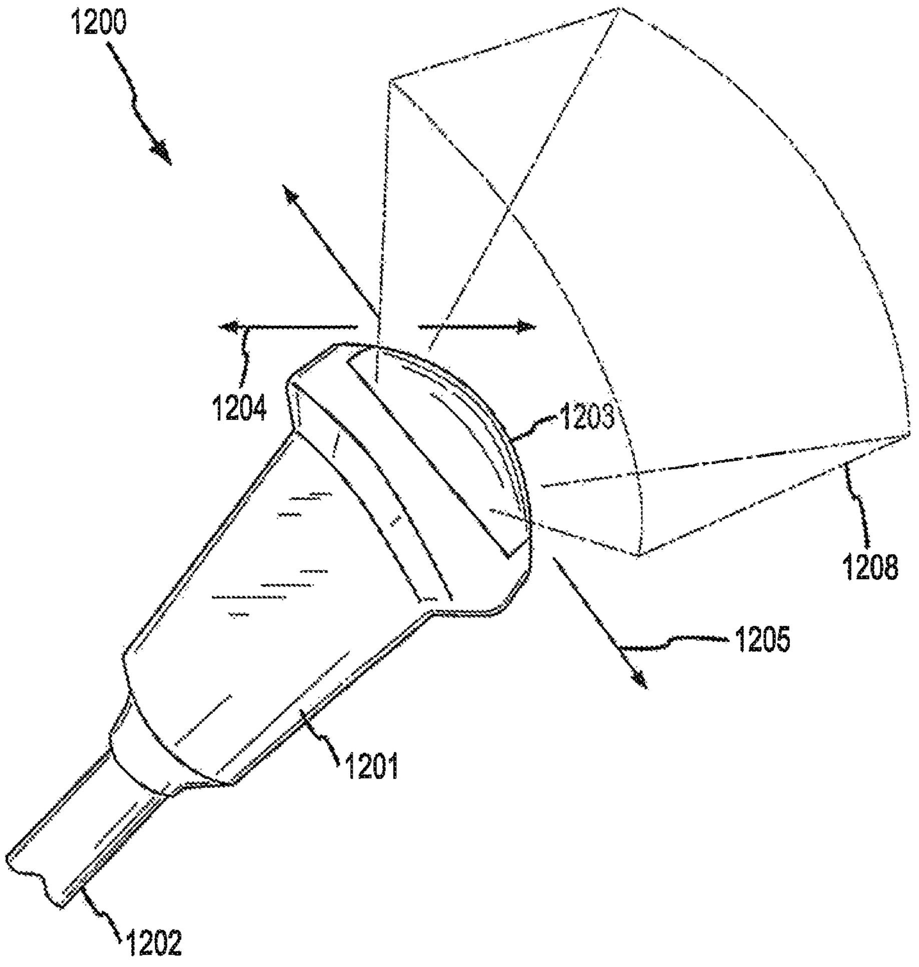
FIG. 2 is an isometric view of an embodiment of an ultrasound probe of the present invention.

FIG. 2 illustrates a perspective view of one particular embodiment of an ultrasound probe assembly 1200. The probe assembly 1200 includes a housing 1201 and a cable 1202. The cable 1202 is interconnected to an ultrasound imaging apparatus (not shown). Generally, the probe assembly 1200 includes a plurality of ultrasonic transducers contained within the housing 1201 and operable to transmit ultrasonic energy through a probe assembly face 1203 along one end of the probe assembly 1200. The ultrasonic energy, in the form of acoustic waves, may be directed through the outer surface of a patient and into the internal structure of the patient. The acoustic waves may interact with and reflect off of various internal features. These reflections may then be detected by the probe assembly 1200 and displayed as images of the internal structure of the patient by the ultrasound imaging apparatus.

The probe assembly 1200 may be operable to scan an imaging volume 1208. This may be accomplished by mounting a one-dimensional transducer array on a movable member. Generally, one-dimensional transducer arrays include a single row containing a plurality of transducer elements along a longitudinal axis 1205. Through electronic control, a beam of acoustic energy may be swept along the longitudinal axis 1205. Some of the acoustic energy is reflected back to the transducer array where it is converted by the transducer array from acoustic energy to electrical signals. These electrical signals may then be converted into a two-dimensional image of the area swept by the acoustic energy. The probe assembly 1200 may contain a one-dimensional transducer array that may be mechanically swept (e.g., rotated) along an elevation axis 1204. Thus, through a combination of electronic sweeping along a longitudinal axis 1205 and mechanical sweeping of the transducer array along an elevation axis 1204, a beam of acoustic energy may be swept through the imaging volume 1208. Energy reflected back to the transducer array may be converted into a three-dimensional image of the imaging volume 1208.

The transducer array in probe assembly 1200 may also be a two-dimensional array that may be mechanically swept (e.g., rotated) along an elevation axis 1204. The dimension of the array perpendicular to the axis of rotation (e.g., the elevation axis 1204) may be utilized to further control the transmitted acoustic energy. For example, transducers along the elevation axis 1204 may be used to shape the acoustic energy to reduce side lobes and improve focus along the elevation axis 1204.

Figure 3:
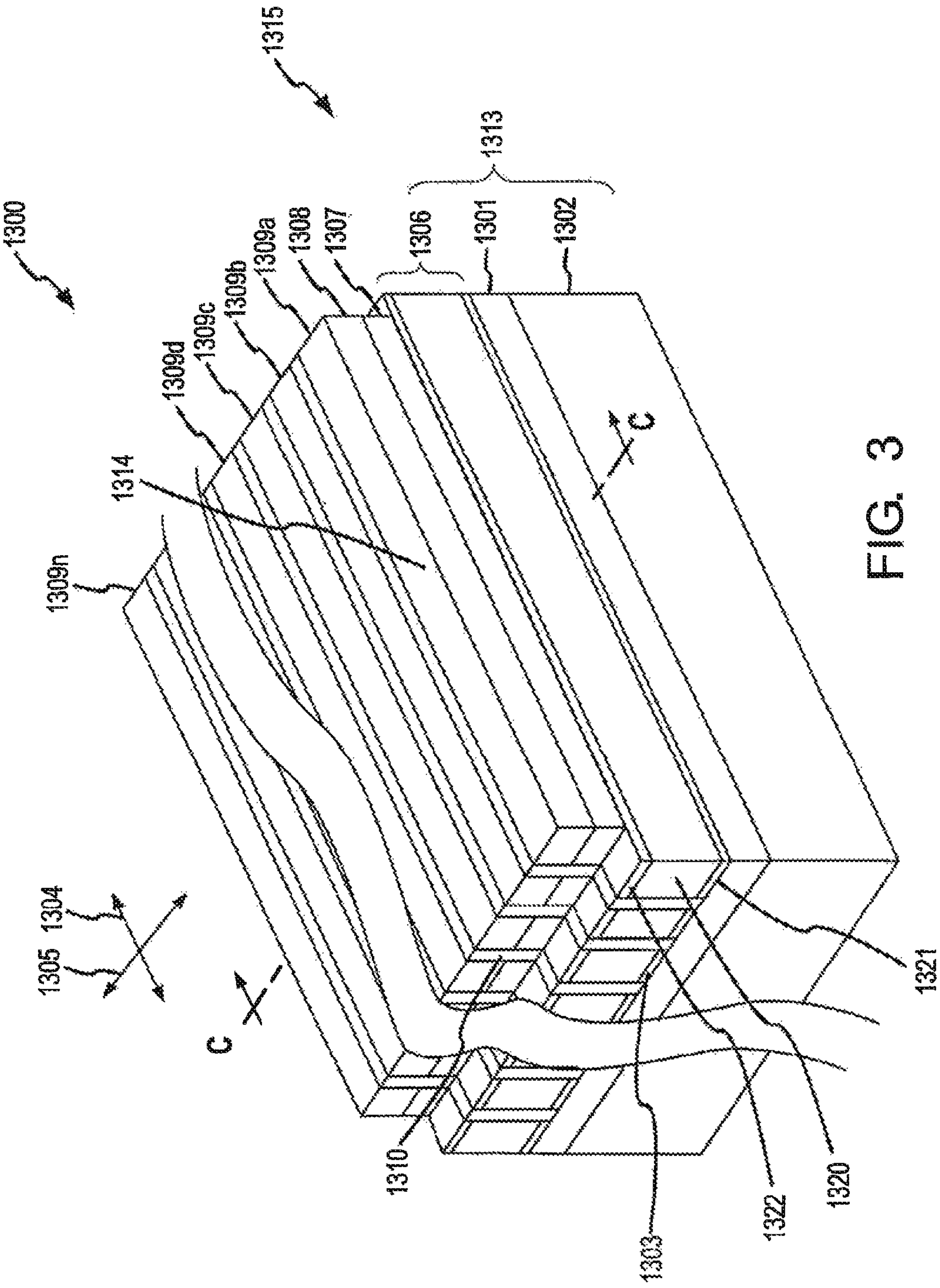
FIG. 3 is a schematic view of a portion of the ultrasonic transducer of FIG. 2.

Turning to FIG. 3, a cross-sectional schematic view of a one-dimensional ultrasonic transducer system 1300 is presented. The ultrasonic transducer system 1300 has a longitudinal axis 1305 and an elevation axis 1304, which, for example, are similar to the longitudinal axis 1205 and elevation axis 1204, respectively, of the probe assembly of FIG. 2. The ultrasonic transducer system 1300 may be operable to transmit and/or receive ultrasonic signals.

Generally, as known to those skilled in the art, a transducer 1315 (comprising an active layer such as piezoelectric layer 1306 and any optional matching layer attached thereto described below) may be divided into a predetermined number of discrete sections (for example, sections 1309*a* through 1309*n*, where n represents the predetermined number of discreet sections) along the longitudinal axis 1305. Each of these discrete sections may be a transducer element (e.g., discrete section 1309 a may be a transducer element). The discrete sections may be electrically interconnected so that two or more of the discrete sections operate as a single transducer element (e.g., discrete sections 1309 *a* and 1309 *b* may be electrically interconnected and function as a single transducer element). A backing 1313 may also be present.

FIG. 3 shows the ultrasonic transducer system 1300 as being straight along the longitudinal axis 1305. The ultrasonic transducer system 1300 may be curved along the longitudinal axis 1305. This curvature may, for example, be achieved by placing individual planar transducer elements at angles to each other along the longitudinal axis 1305. FIG. 3 also shows the individual transducer elements of the ultrasonic transducer system 1300 as planar along the elevation axis 1304. In an alternative configuration, the individual transducer elements of the ultrasonic transducer system 1300 may be curved along the elevation axis 1304.

The transducer 1315 may include a piezoelectric layer 1306. The piezoelectric layer 1306 may include a layer of piezoelectric material 1320, a first electrode layer 1321 and a second electrode layer 1322. The layer of piezoelectric material 1320 may include a ceramic-based material (e.g., lead zirconate titanate (PZT)). The first electrode layer 1321 and second electrode layer 1322 may include one or more layers of electrically conductive material. The portion of the first electrode layer 1321 connected to each individual transducer element may serve as the signal electrode for that individual transducer element. Similarly, the portion of the second electrode layer 1322 connected to each individual transducer element may serve as the ground electrode for that individual transducer element.

Generally, the signal electrodes and ground electrodes are arranged as illustrated in FIG. 3 with the ground electrode on the side of the piezoelectric material 1320 that faces the region to be imaged. The position of the signal and ground electrodes may be reversed. In such embodiments, it may be necessary to provide an additional grounding layer to shield the signal layer. The ground electrodes may be individual electrodes as illustrated in FIG. 3 or may be one continuous layer of grounding material situated over each of the individual transducer elements. The individual transducer element electrodes may be interconnected to electronic circuitry, which may provide for acoustic wave generation and sensing.

Optional acoustic matching layers may be interconnected to the piezoelectric layer 1306. The ultrasonic transducer system 1300 of FIG. 3 shows a first optional matching layer 1307 and a second optional matching layer 1308 interconnected to the piezoelectric layer 1306. The presence and number of optional matching layers may vary from the configuration illustrated in FIG. 3. The transducer 1315 comprises the piezoelectric layer 1306, along with any optional matching layers attached thereto.

The piezoelectric layer 1306 may be a mechanically active layer operable to convert electrical energy to mechanical energy and mechanical energy into electrical energy. As previously described, the piezoelectric layer 1306 may include a layer of PZT material sandwiched between ground and signal electrodes. A variety of components and materials able to generate acoustic signals may be substituted for at least a portion of the piezoelectric layer 1306. Such components and materials include ceramic materials, ferroelectric materials, composite materials, capacitor micromachined ultrasound transducers (CMUTs), piezoelectric micromachined ultrasound transducers (PMUTs), and any combination thereof. Regardless of the specific components, electromechanical principle of operation or materials, the mechanically active layer may comprise a means of converting electrical energy to mechanical energy and mechanical energy into electrical energy, which has an acoustic face 1314 and a plurality of transducer elements that may be controlled individually. Generally, any system known to those skilled in the art for generating ultrasonic acoustic signals that may be used for imaging purposes may be utilized in the mechanically active layer.

Each individual discrete section may be separated from neighboring discrete sections by kerfs (e.g., kerf 1310 between discrete sections 1309 *c* and 1309 *d*) produced during the dicing of the transducer 1315. The kerfs may be filled with a filler material. Additionally, one or more acoustic lenses may be interconnected to the acoustic face 1314.

As the piezoelectric layer 1306 emits acoustic energy, some acoustic energy will pass into the backing 1313. Since such acoustic energy is not directed to the imaging volume 1208, it is desirable that this acoustic energy be attenuated. Attenuating this acoustic energy helps to reduce the amount of acoustic energy being reflected back into the piezoelectric layer 1306 through the back side of the piezoelectric layer 1306. Such reflected acoustic energy may interfere with the acoustic energy being reflected back to the piezoelectric 1306 from the imaging volume 1208, which may result in image degradation.

In the illustrated embodiment, the backing 1313 includes multiple layers (e.g., first layer 1301 and second layer 1302). Of course, it should be understood that the backing 1313 may also be formed of a single layer. Regardless, at least a portion of the backing 1313 may contain the polymer composition of the present invention to serve as an acoustic attenuation material. In one embodiment, for instance, the second layer 1302 and/or first layer 1301 may be formed from the polymer composition. Of course, such layers may also contain other materials known to those skilled in the art of ultrasonic transducer design, such as, for example epoxy resins, silicone rubber, tungsten, aluminum oxide, mica, microspheres, or a combination thereof.

The components of the ultrasonic probe that are formed from the polymer composition (e.g., backing, housing, etc.) may be formed using a variety of different techniques. Suitable techniques may include, for instance, injection molding, low-pressure injection molding, extrusion compression molding, gas injection molding, foam injection molding, low-pressure gas injection molding, low-pressure foam injection molding, gas extrusion compression molding, foam extrusion compression molding, extrusion molding, foam extrusion molding, compression molding, foam compression molding, gas compression molding, etc. For example, an injection molding system may be employed that includes a mold within which the polymer composition may be injected. The time inside the injector may be controlled and optimized so that polymer matrix is not pre-solidified. When the cycle time is reached and the barrel is full for discharge, a piston may be used to inject the composition to the mold cavity. Compression molding systems may also be employed. As with injection molding, the shaping of the polymer composition into the desired article also occurs within a mold. The composition may be placed into the compression mold using any known technique, such as by being picked up by an automated robot arm. The temperature of the mold may be maintained at or above the solidification temperature of the polymer matrix for a desired time period to allow for solidification. The molded product may then be solidified by bringing it to a temperature below that of the melting temperature. The resulting product may be de-molded. The cycle time for each molding process may be adjusted to suit the polymer matrix, to achieve sufficient bonding, and to enhance overall process productivity.

The present invention may be better understood with reference to the following example.

Test Methods

Thermal Conductivity: In-plane and through-plane thermal conductivity values are determined in accordance with ASTM E1461-13.

Melt Viscosity: The melt viscosity (Pa-s) may be determined in accordance with ISO Test No. 11443:2005 at a shear rate of 400 $s^{-1}$ and temperature 45° C. above the melting temperature (e.g., about 305° C.) using a Dynisco LCR7001 capillary rheometer. The rheometer orifice (die) had a diameter of 1 mm, length of 20 mm, L/D ratio of 20.1, and an entrance angle of 180°. The diameter of the barrel was 9.55 mm+0.005 mm and the length of the rod was 233.4 mm.

Melting Temperature: The melting temperature ("Tm") may be determined by differential scanning calorimetry ("DSC") as is known in the art. The melting temperature is the differential scanning calorimetry (DSC) peak melt temperature as determined by ISO Test No. 11357-2:2013. Under the DSC procedure, samples were heated and cooled at 20° C. per minute as stated in ISO Standard 10350 using DSC measurements conducted on a TA Q2000 Instrument.

Deflection Temperature Under Load ("DTUL"): The deflection under load temperature may be determined in accordance with ISO Test No. 75-2:2013 (technically equivalent to ASTM D648-07). More particularly, a test strip sample having a length of 80 mm, thickness of 10 mm, and width of 4 mm may be subjected to an edgewise three-point bending test in which the specified load (maximum outer fibers stress) was 1.8 Megapascals. The specimen may be lowered into a silicone oil bath where the temperature is raised at 2° C. per minute until it deflects 0.25 mm (0.32 mm for ISO Test No. 75-2:2013).

Tensile Modulus, Tensile Stress, and Tensile Elongation: Tensile properties may be tested according to ISO Test No. 527:2012 (technically equivalent to ASTM D638-14). Modulus and strength measurements may be made on the same test strip sample having a length of 80 mm, thickness of 10 mm, and width of 4 mm. The testing temperature may be 23° C., and the testing speeds may be 1 or 5 mm/min.

Flexural Modulus, Flexural Stress, and Flexural Elongation: Flexural properties may be tested according to ISO Test No. 178:2010 (technically equivalent to ASTM D790-10). This test may be performed on a 64 mm support span. Tests may be run on the center portions of uncut ISO 3167 multi-purpose bars. The testing temperature may be 23° C. and the testing speed may be 2 mm/min.

Unnotched Charpy Impact Strength: Charpy properties may be tested according to ISO Test No. ISO 179-1:2010) (technically equivalent to ASTM D256-10, Method B). This test may be run using a Type 1 specimen size (length of 80 mm, width of 10 mm, and thickness of 4 mm). The testing temperature may be 23° C.

EXAMPLE

A polymer composition for use in an ultrasonic probe may be formed from 55 wt. % graphite flakes and 45 wt. % of a liquid crystalline polymer as described herein. The composition may exhibit the thermal and mechanical properties set forth in the table below.

| | |
|---|---|
| Tensile Modulus (GPa) | 7.1 |
| Tensile Strength (MPa) | 32 |
| Tensile Elongation at Break (%) | 0.7% |
| Flexural Modulus (GPa) | 11.1 |
| Flexural Strength (MPa) | 56 |
| Charpy Unnotched Impact Strength at 23° C. (kJ/m$^2$) | 3.4 |
| Thermal Conductivity, In-plane, flow direction (W/mK) | 34 |
| Thermal conductivity, through-plane (W/mK) | 4.5 |
| DTUL at 1.8 MPa (° C.) | 198 |

These and other modifications and variations of the present invention may be practiced by those of ordinary skill in the art, without departing from the spirit and scope of the present invention. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. An ultrasonic probe comprising:

an ultrasonic transducer that includes an array of transducer elements capable of converting electrical energy to ultrasonic acoustic energy for emission towards a region of interest; and an attenuation material that is capable of inhibiting the return of the ultrasonic acoustic energy back towards the ultrasonic transducer after emission towards the region of interest, wherein the attenuation material comprises a polymer composition that includes a liquid crystalline polymer and a thermally conductive particulate material, wherein the liquid crystalline polymer comprises repeating units derived from naphthenic hydroxycarboxylic acids and/or naphthenic dicarboxylic acids has a melting temperature of about 270° C. or more and a melt viscosity of about 500 Pa-s or less as determined at a temperature of 45° C. above the melting temperature and shear rate of 400 s$^{-1}$ in accordance with ISO Test No. 11443:2005, and further wherein the polymer composition has a through-plane conductivity of 0.4 W/m-K or more.

2. The ultrasonic probe of claim 1, wherein the liquid crystalline polymer comprises repeating units (1) to (3):

(1)

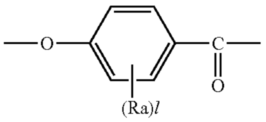

(2)

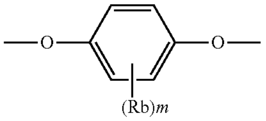

(3)

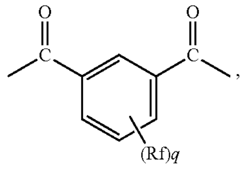

wherein,

Ra, Rb, and Rf are independently alkynyl, alkyl, alkenyl, aryl, heteroaryl, cycloalkyl, heterocyclyl, halo, or haloalkyl; and l, m, and q are independently an integer from 0 to 4.

3. The ultrasonic probe of claim 2, wherein the repeating units (1) are derived from 4-hydroxybenzoic acid, the repeating units (2) are derived from hydroquinone, and the repeating units (3) are from isophthalic acid.

4. The ultrasonic probe of claim 2, wherein the repeating units (1) constitute from about 40 mole % to about 80 mole % of the polymer, and wherein the repeating units (2) and (3) each constitute from about 1 mole % to about 20 mole % of the polymer.

5. The ultrasonic probe of claim 2, wherein the molar ratio of repeating units (2) to the repeating units (3) is from about 0.8 to about 2.

6. The ultrasonic probe of claim 2, wherein the liquid crystalline polymer further comprises repeating units (4) and (5):

(4)

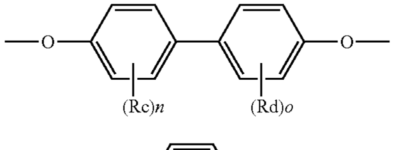

(5)

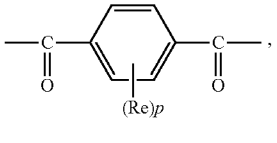

wherein,

Rc, Rd, and Re are independently alkynyl, alkyl, alkenyl, aryl, heteroaryl, cycloalkyl, heterocyclyl, halo, or haloalkyl; and n, o, and p are independently an integer from 0 to 4.

7. The ultrasonic probe of claim 6, wherein the repeating units (4) are derived from 4,4'-biphenol and the repeating units (5) are derived from terephthalic acid.

8. The ultrasonic probe of claim 7, wherein the repeating units (4) and (5) each constitute from about 5 mole % to about 30 mole % of the polymer.

9. The ultrasonic probe of claim 7, wherein the molar ratio of repeating units (5) to the repeating units (4) is from about 0.8 to about 2.

10. The ultrasonic probe of claim 1, wherein the thermally conductive particulate material has an average size of about 100 to about 2,000 micrometers.

11. The ultrasonic probe of claim 1, wherein the thermally conductive particulate material has an intrinsic thermal conductivity of about 50 W/m-K or more.

12. The ultrasonic probe of claim 1, wherein the thermally conductive particulate material includes boron nitride, aluminum nitride, magnesium silicon nitride, graphite, silicon carbide, carbon nanotubes, carbon black, metal oxide, metallic powder, or a combination thereof.

13. The ultrasonic probe of claim 1, wherein the thermally conductive particulate material is present in the polymer composition in an amount of from about 50 to about 200 parts per 100 parts of the liquid crystalline polymer.

14. The ultrasonic probe of claim 1, wherein the thermally conductive particulate material constitutes from about 25 wt. % to about 70 wt. % of the polymer composition and liquid crystalline polymers constitute from about 30 wt. % to about 75 wt. % of the polymer composition.

15. The ultrasonic probe of claim 1, wherein the polymer composition has a through-plane conductivity of from about 4 to about 15 W/m-K.

16. The ultrasonic probe of claim 1, wherein the ultrasonic probe is connected to an ultrasound imaging apparatus that is configured to send the electrical energy to the ultrasonic transducer.

17. The ultrasonic probe of claim 1, wherein the attenuation material is electrically connected to a surface of the ultrasonic transducer.

18. The ultrasonic probe of claim 1, further comprising a housing that encloses the ultrasonic transducer.

19. The ultrasonic probe of claim 18, wherein at least a portion of the housing is formed from the attenuation material.

20. The ultrasonic probe of claim 19, wherein the attenuation material is positioned on a surface of the housing.

21. The ultrasonic probe of claim 1, wherein the ultrasonic transducer includes a piezoelectric layer positioned adjacent to a backing.

22. The ultrasonic probe of claim 21, wherein the backing includes the attenuation material.

* * * * *